(12) United States Patent
Brodnick (10) Patent No.: US 6,918,878 B2
(45) Date of Patent: Jul. 19, 2005

(54) METHODS AND SYSTEMS FOR MONITORING RESPIRATION

(75) Inventor: Donald E. Brodnick, Cedarburg, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 43 days.

(21) Appl. No.: 10/460,972

(22) Filed: Jun. 13, 2003

(65) Prior Publication Data

US 2004/0254481 A1 Dec. 16, 2004

(51) Int. Cl.[7] .................................................. A61B 5/00
(52) U.S. Cl. ...................... 600/483; 600/500; 600/586; 600/529
(58) Field of Search .......................... 600/528, 529–538, 600/586

(56) References Cited

U.S. PATENT DOCUMENTS

| | | | |
|---|---|---|---|
| RE27,042 E | 1/1971 | Jorgensen et al. | |
| 5,143,078 A | 9/1992 | Mather et al. | |
| 5,218,969 A | 6/1993 | Bredesen et al. | |
| 5,957,866 A | 9/1999 | Shapiro et al. | |
| 6,064,910 A | * 5/2000 | Andersson et al. | ............ 607/20 |
| 6,517,497 B2 | 2/2003 | Rymut et al. | |
| 6,739,335 B1 | * 5/2004 | Rapport et al. | ......... 128/204.18 |
| 2001/0025137 A1 | * 9/2001 | Webb et al. | ................ 600/300 |
| 2002/0035337 A1 | 3/2002 | Oka | |
| 2002/0058889 A1 | 5/2002 | Lee | |
| 2002/0072685 A1 | 6/2002 | Rymut et al. | |
| 2003/0093002 A1 | * 5/2003 | Kuo | ............................ 600/528 |
| 2003/0095263 A1 | * 5/2003 | Varshneya et al. | ........... 356/477 |
| 2003/0120164 A1 | 6/2003 | Nielsen et al. | |
| 2003/0220584 A1 | * 11/2003 | Honeyager et al. | .......... 600/559 |

* cited by examiner

Primary Examiner—Robert L. Nasser
(74) Attorney, Agent, or Firm—Andrus, Sceales, Starke & Sawall, LLP (57) ABSTRACT

A method for determining respiration rate in a patient can include various parts. The respiration rate can be determined by measuring the heart's S2 split. The S2 split can be identified by observing the timing of the heart sounds. Other respiration related information, such as respiration phase and the occurrence of apnea, can be identified as well. A respiration monitor of this type may be useful for monitoring sub-acute patients, and outpatients. A sensor for the respiration monitor and an electrode for an ECG monitor may be combined into a single probe.

39 Claims, 6 Drawing Sheets

METHODS AND SYSTEMS FOR MONITORING RESPIRATION

BACKGROUND

Respiration is the process by which animals inhale and exhale oxygen. In this process, oxygen and carbon dioxide are typically exchanged in the lungs. This process is important for most land animals, as respiration is typically involved in the only process by which animals incorporate oxygen, an essential molecule for the proper functioning of the body.

Figure 1:
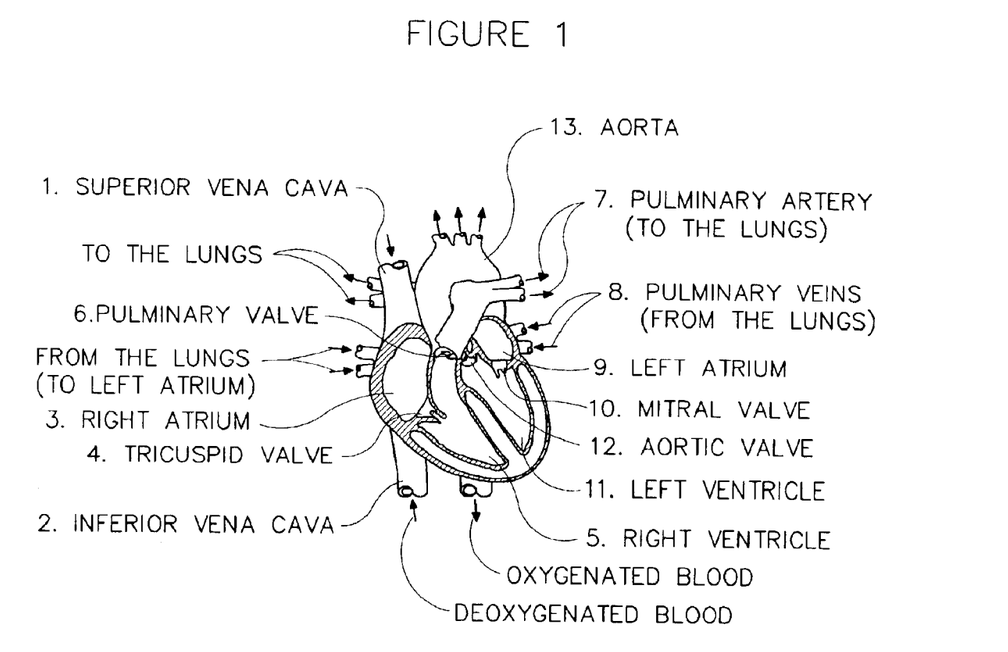
FIG. 1 is a diagram illustrating components in the circulation system of a person.

With reference to FIG. 1, the human heart is composed of four chambers; the right and left atria and the right and left ventricles. Each chamber of the heart has a valve at its exit such that blood passing through the valve is largely prevented from going back in to that chamber. The Superior Vena Cava 1 collects blood from the upper half of the body. The Inferior Vena Cava 2 collects blood from the lower half of the body. Blood leaves the Superior Vena Cava 1 and the Inferior Vena Cava 2 and enters the Right Atrium 3. Blood entering the Right Atrium 3 is generally deoxygenated blood. When the Right Atrium 3 contracts, the blood goes through the Tricuspid Valve 4 and into the Right Ventricle 5. When the Right Ventricle 5 contracts blood is pumped through the Pulmonary Valve 6, into the Pulmonary Artery 7 and then to the lungs where it picks up oxygen.

Blood returns to the heart from the lungs by way of the Pulmonary Veins 8 and goes into the Left Atrium 9. When the Left Atrium 9 contracts, blood travels through the Mitral Valve 10 and into the Left Ventricle 11. The Left Ventricle 11 is the chamber that pumps blood through the Aortic Valve 12 and into the Aorta 13 to the rest of the body. The Aorta is the main artery of the body, and receives all the blood that the heart has pumped out and distributes it to the rest of the body. The Left Ventricle 11 typically has a thicker muscle than any other heart chamber because it must pump blood to the rest of the body against much higher pressure in the general circulation (blood pressure).

The Left and Right Atria generally contract at about the same time. Also, the Left and Right Ventricles generally contract at about the same time. This generally leads to a nearly synchronous opening and closing of the Tricuspid Valve 4 and the Mitral Valve 10, and a nearly synchronous opening and closing of the Pulmonary Valve 6 and Aortic Valve 12. When the valves close, they tend to make generally lower frequency sounds. These sounds generally contribute to the "thump, thump" sound typically associated with the heart; the closing of the atrial valves being the first "thump", and the closing of the ventriclular valves being the second "thump". Since the atria-closing valves generally occur at about the same time and since the ventricle-closing valves generally occur about the same time, the closing of the four valves generally only leads to two sounds. These sounds are classified as the S1 (the atria-closing sound) and the S2 (the ventricle-closing sound).

These sounds can be harnessed to give any number of medically relevant information. For instance, if one or more of the heart valves are not operating properly, the S1 or S2 sounds may be skewed, diminished, or not present. Since these sounds are easily identifiable using non-invasive procedures, it would be advantageous to develop systems that could take advantage of these sounds to develop medically relevant information.

It is often desirable to know a patient's respiratory rate, such as for a patient under anesthesia. If the respiratory rate falls dramatically, is erratic, or is non-existent, the patient may be suffering serious complications that need to be addressed. A system that can be used to measure respiration rate would be advantageous, especially if that system could rely on a non-invasive procedure such as monitoring heart sounds.

Monitoring physiological signals is generally done by measuring the amplitude of some variable, measuring the frequency at which some variable occurs, by measuring the time at which some variable occurs, or, more commonly, some combination of those factors. Not every physiological variable is susceptible to measurement by each of these techniques. When measuring variables by amplitude, noise can often be a problem. A patient who moves or has other monitoring equipment which introduces noise into the relevant monitor will often have amplitudes that vary erratically, or have noise effects that prevents fully accurate measurements from being made. These noise effects can sometimes be compensated, but often at the expense of the simplicity and sometimes the accuracy of the system. A system that does not need to rely on amplitude measurements to identify a physiologic data would be preferable.

Also, some patients may have multiple monitors and other medical devices connected to the patient at any one time. Some of these monitors and medical devices may use technologies or techniques that may interfere with the accuracy of other monitors or devices. It would be preferable to use a monitoring system that would not interfere with other monitors and devices. Also, it would be preferable to have a monitoring system that is generally not greatly affected by the presence of other monitors or medical devices.

While it is generally advantageous to measure respiration rate, many current respiration rate monitors tend to be cost-prohibitive for many patients. The amount of money available to be spent on the care of sub-acute patients (patients with less severe conditions) is generally less than that for patients with more severe conditions because monitoring of some sub-acute patients is typically considered more precautionary than critical. Thus, monitors that are relatively expensive or cumbersome are usually reserved for patients with conditions that are more severe. It would be desirable to have a respiration monitor that is less expensive. Additionally, it would be preferable to have a respiration monitor that is not very bulky.

Those patients who are monitored more heavily typically have a large number of separate machines connected to them at any one time. This increase in the number of machines increases the clutter associated with the heavily monitored patients. A system that could reduce the number of machines needed to monitor a patient would be advantageous.

The teachings hereinbelow extend to those embodiments which fall within the scope of the appended claims, regardless of whether they accomplish one or more of the above-mentioned needs.

SUMMARY OF THE INVENTION

One embodiment is directed to a method for determining respiration rate. The method includes obtaining heart sounds from a patient, and determining respiration rate based on timing of the heart sounds.

Another embodiment provides a method for determining respiration rate in a patient having an S2 split. The method includes identifying a duration of an S2 split, and determining respiration rate based on the duration of the S2 split.

Another embodiment relates to a method for identifying respiration related information, such as the occurrence of apnea, based on timing of the heart characteristics such as the timing of the S2 split and the sounds produced by the heart. The method can include measuring heart sounds and/or measuring the S2 split with or without using heart sounds. This information can be used to identify a patient's respiration rate, heart rate, respiration related conditions (such as apnea), respiration phase, heart related conditions, etc.

Another embodiment is directed to a medical monitoring system. The system includes an input configured to receive signals from a heart acoustic sensor; and a processing circuit configured to determine respiration rate based on heart sounds input from the heart acoustic sensor. The system can also include a heart acoustic sensor such as a microphone. In one embodiment the sensor is a piezo sensor. The heart acoustic sensor can be coupled to an ECG electrode, such that placement of the sensor is accomplished at the same time as placement of the ECG electrode. The system can also include a band-pass filter that removes non-heart sound frequencies from the signal being input.

An additional embodiment is directed to a system for measuring respiration. The system includes an input that receives a signal relating to an S2 split, and a processing circuit that process the information to provide one or more pieces of respiration related information such as respiration rate, respiration phase, respiration related conditions, etc.

Other principle features and advantages of the invention will become apparent to those skilled in the art upon review of the following drawings, the detailed description, and the appended claims.

DETAILED DESCRIPTION OF THE PREFERRED EMBODIMENTS

It has been found that as a person inhales, the pulmonary valve and the aortic valve tend to close less synchronously, the aortic valve tending to close before the pulmonary valve. This causes the S2 sound to split into two individually identifiable sounds, which sounds still occur close in time to each other. The difference in time between the closing of the pulmonary and aortic valves can be referred to as the duration of the S2 split. As a person respires, a characteristic pattern can be seen in the duration of the S2 split. This pattern can be used to determine a subject's respiration rate, phase of respiration, and other respiration related information such as the presence of respiration related conditions.

Figure 2:
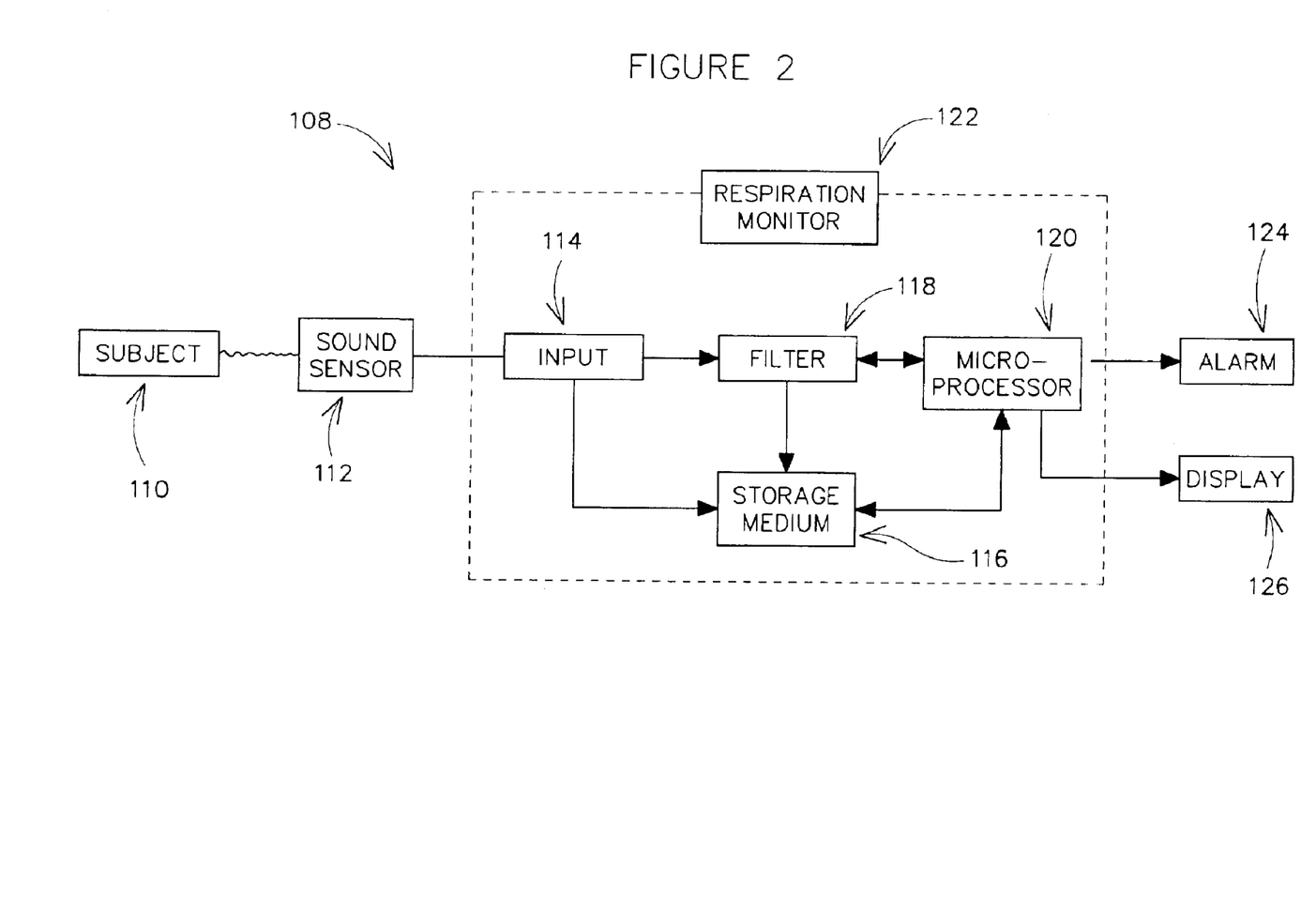
FIG. 2 is a schematic diagram of a monitoring system according to one embodiment.

Referring to FIG. 2, a monitoring system 108 includes an acoustic sensor 112 that obtains sounds from a subject 110. Acoustic sensor 112 is preferably a piezo sensor placed in a location that can be used to obtain heart sounds from a patient. A piezo sensor can be configured to be passive, injecting no currents or other radiations. The piezo film could be configured to produce a broadband voltage output responsive to flexing of the film which is principally responding to sound pressure waves.

Some potential locations for placing the acoustic sensor include anywhere in the sternal area between intercostal space two (ICS-2) and intercostal space four (ICS-4). For instance, since the S2 sound depends on pulmonary valve closing a sensor may be placed at the left sternal border at ICS-2 of a patient where that sound tends to be more easily identified. Also, since the S2 sound depends on aortic valve closing a sensor may be placed at the right sternal border at ICS-2 of a patient where that sound tends to be more easily identified. Further, more than one sensor may be used to identify the S2 sounds.

Signals from acoustic sensor 112 are input to respiration monitor 122 using data input 114. The data received at data input 114 may be filtered by filter 118, processed by microprocessor 120, or stored in data storage medium 116. Filter 118 is preferably a band pass filter (one or more filters which can be used to isolate a band of frequencies) that is configured to isolate the sounds associated with the heart. Filter 118 can be configured to isolate sounds having a frequency, for example, in the range of about 50 Hz to about 1000 Hz, or more narrowly about 100 Hz to about 500 Hz. The data can be samples at somewhere in the range of about 50 to 4000 samples per second (SPS). Filtering the data may eliminate sounds not associated with the heart sounds such as talking and other sounds. Filter 118 can be an analog filter, a digital filter, a demodulator, or some other type of filter. Further, filter 118 may be composed of one or more circuits working independently or in cooperation.

Microprocessor 120 can be configured to process the signals to identify respiration related information based on the data input from acoustic sensor 112. Microprocessor 120 may be configured to perform pattern recognition, determine the S2 split duration and/or identify a duration trend. Alternatively data may be stored in data storage medium 116 which can later be downloaded to a separate processor. Additionally, data may be partially processed by microprocessor 120, and then stored in data storage medium 116 to be processed further at a later point in time.

Data from respiration monitor 122 may be output to a display 126 to display respiration related information. Respiration related information that may be displayed includes respiration rate, respiration phase, whether respiration rate is within normal limits, the presence (or potential presence) of an apnea event, the type of apnea present, etc. Information may be displayed visually, using an audible signal (a tone, a simulated voice, etc.), or in some other manner. Display 126 may be in the form of a bed-side monitor, a personal computing device, a remote monitor, or other display device.

The data may also be used to initiate an alarm 124. The alarm may be in the vicinity of respiration monitor 122, or may be remote from respiration monitor 122 (such as at a nurse's station, or in the form of a pager or personal computing device carried by a clinician).

Figure 5:
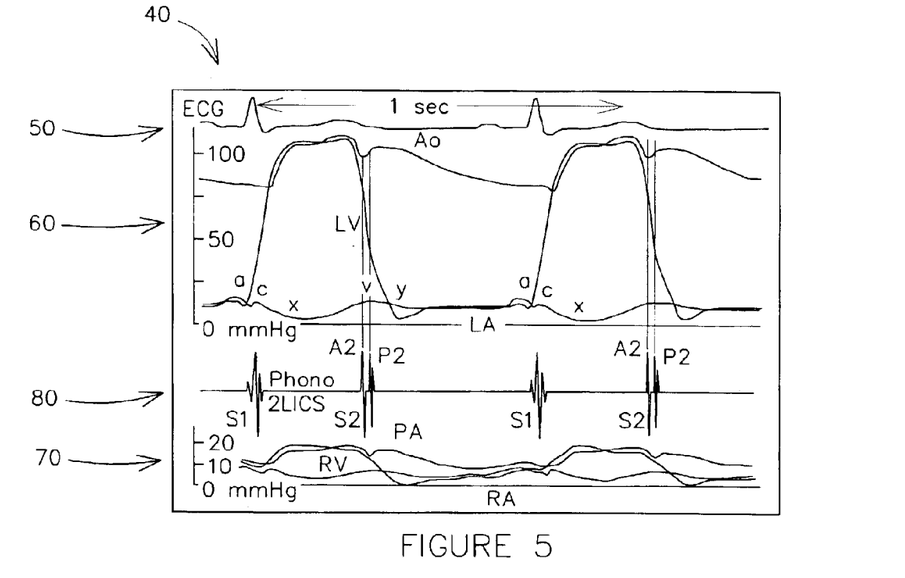
FIG. 5 is a graphic representation of various typical physiological data, including heart sounds, at the beginning of inspiration.
Figure 6:
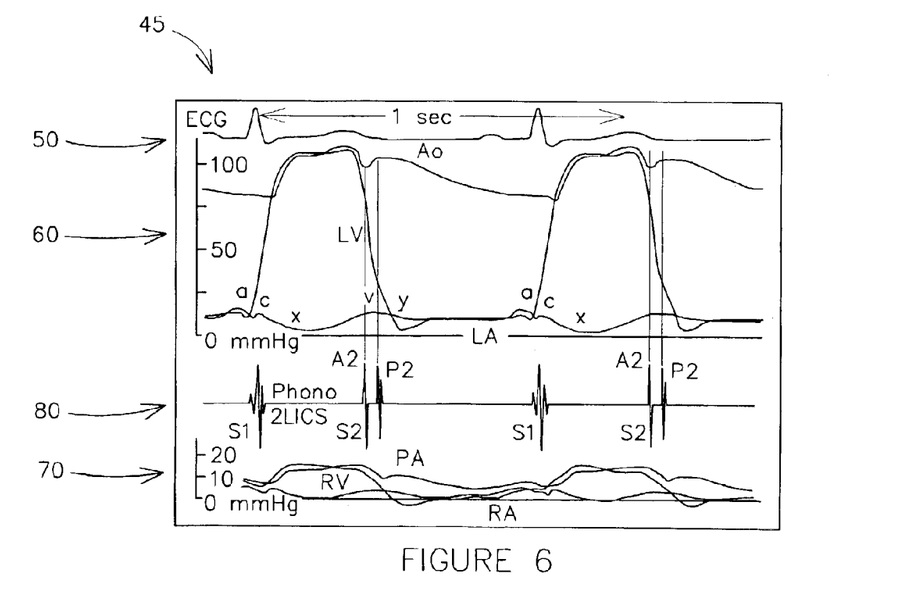
FIG. 6 is a graphic representation of various typical physiological data, including heart sounds, at the end of inspiration.

Referring to FIGS. 5 and 6, a representation 40 of typical physiological data from a patient at the end of respiration includes a representation of ECG data 50, left chamber pressure data 60, right chamber pressure data 70, and heart sound data 80. A representation 45 of typical physiological data from a patient at the end of inspiration (breathing in)

includes a representation of ECG data 50, left chamber pressure data 60, right chamber pressure data 70, and heart sound data 80. Left chamber pressure data includes left ventricular pressure data (LV), left atrial pressure data (LA), and aortic pressure data (Ao). Right chamber pressure data includes right ventricular pressure data (RV), right atrial pressure data (RA), and pulmonary pressure data (PA). Heart sound data includes the atrial valve sounds (S1) and the ventricular valve sounds (S2). The S2 sound can be divided into the sound caused by the closing of the aortic valve (A2) and the sound caused by the closing of the pulmonary valve (P2).

As can be seen, at the end of expiration (FIG. 5) the S2 split is relatively small, whereas when a patient is at the end of inspiration (FIG. 6) the S2 split is noticeably larger. The duration of the S2 split over a series of measurements can be obtained, and this data can be analyzed to provide information regarding the respiration rate and other related information (such as respiration phase).

Figure 7:
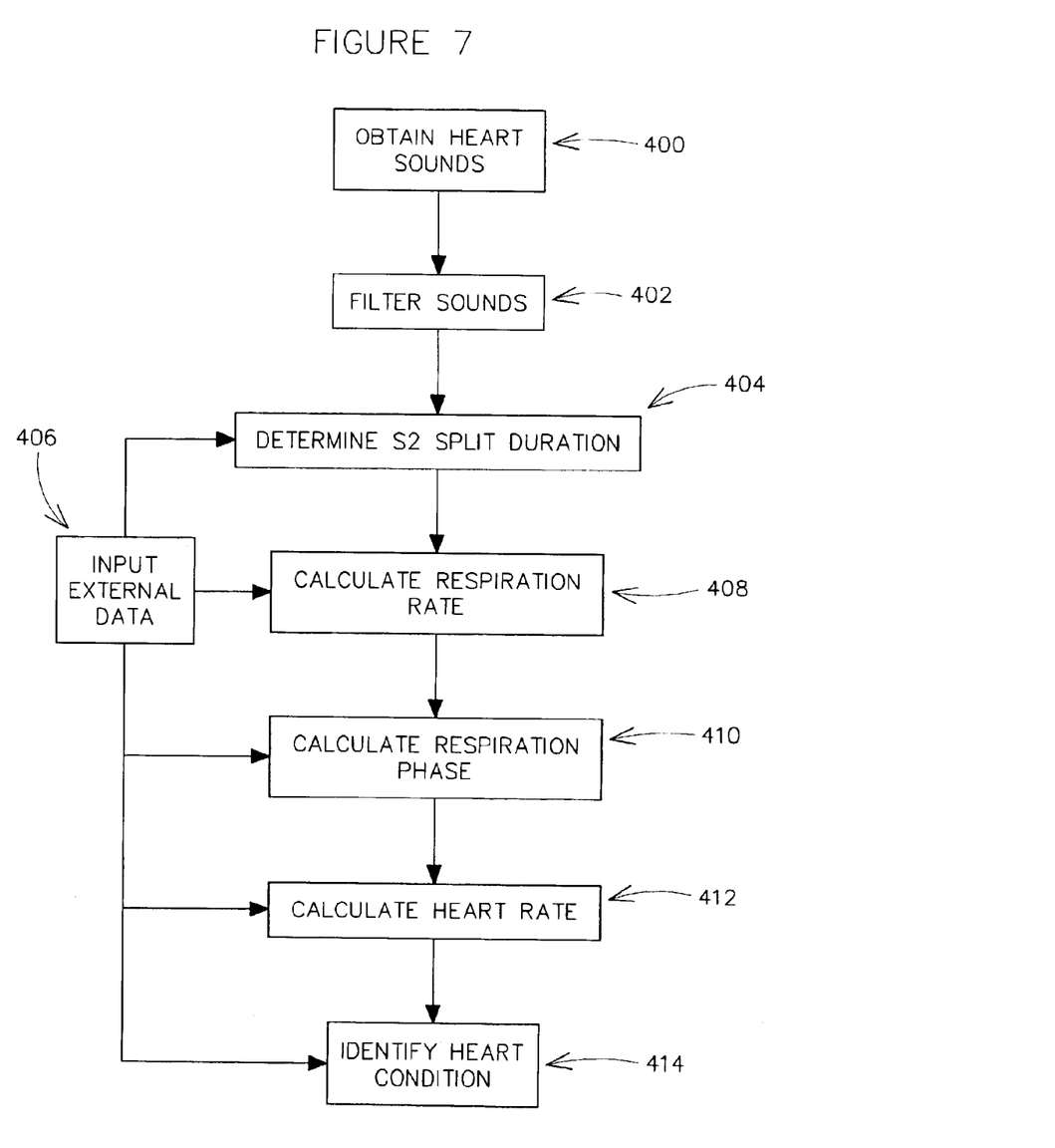
FIG. 7 is a flow chart according to one embodiment.

Referring to FIG. 7, heart sounds are obtained from a acoustic sensor coupled to a subject at block 400. The sounds can be filtered at block 402 to remove noise from the signal, such as sounds having frequencies not associated with heart sounds. The heart sounds can be used to determine the S2 split duration at block 404. Other means may alternatively (or additionally) be used to measure the S2 split duration. For instance, an ultrasound device may be employed to monitor the opening and closing of the aortic and pulmonary valves.

Once the S2 split duration has been determined at block 404, respiration rate related information may be calculated at block 408 based on the S2 split duration. Additionally, the phase of respiration may be determined at block 310 based on the S2 split duration.

Other factors may also be determined using the inputted data. For instance, the acquired data can also be used to calculate heart rate at block 412. One example of this may include using the frequency of occurrence of one of the S2 sounds, the S1 sound, or some other heart sound to calculate the heart rate. Additionally, heart related conditions, or other conditions, may be monitored at block 314 to identify the presence of abnormalities, risk factors, and other heart related information. Examples of some heart related conditions which may be identified at block 414 include various arrhythmias, heart murmurs, heart rate variability (HRV), heart rate turbulence (HRT), extrasystole, asystole, Ventricular tachycardia, Sinus Tachycardia, Sinus Bradycardia, atrial arrhythmias, and/or others.

In addition to using heart sounds and other S2 split related information, other data may be used to obtain useful information at block 406. For example, an independent measurement of heart rate may be used to aid in the determination of the S2 split interval. Additionally, multiple sources of S2 split information may be combined at block 404, and/or multiple sources of respiration rate may be combined at block 408. S2 split duration information may be used to calculate one measure of respiration rate which may then be combined with other sources of respiration rate information (such as impedance pneumography, heart sound amplitude changes, thermistors, air flow transducers, capnography, air flow acoustic sensors, etc.) to determine the most likely respiration related value, and/or a value representing a combination of data from one or more sources. In the same manner, other data can be imported to calculate heart rate at block 412 and identify heart related conditions at block 414.

Figure 8:
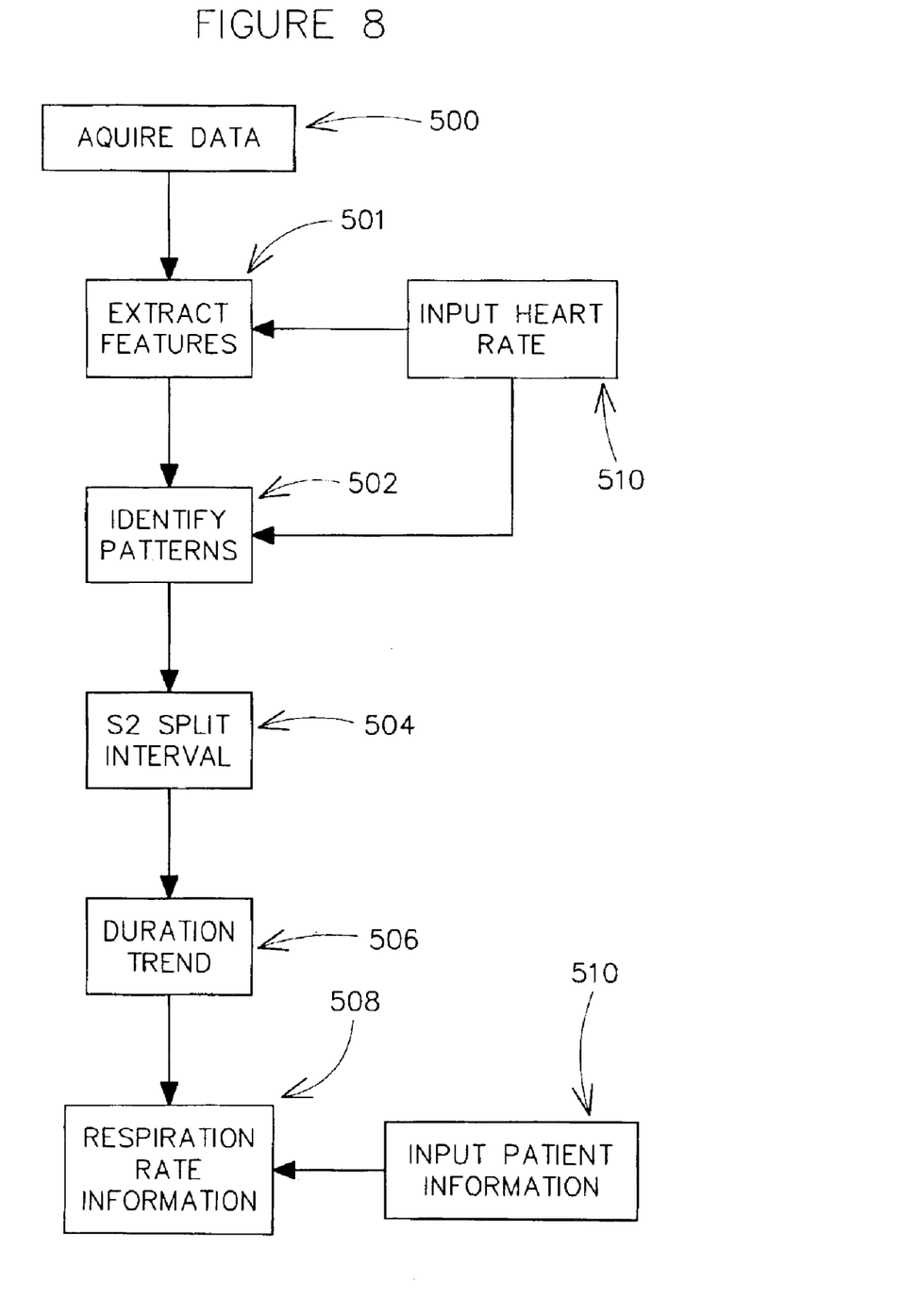
FIG. 8 is a flow chart according to another embodiment.

Referring to FIG. 8, heart sound data is acquired at block 500. The data may be raw data, or may be filtered data. The data is analyzed at blocks 501 and 502 to identify the S2 split. The analysis may involve extracting known features from the data at block 501, and identifying patterns in the data at block 502. The heart rate may be imported at block 510 to aid in the analysis process. Since subsequent S2 data portions of the signal would occur at roughly the same interval as the heart rate, the heart rate could be used to identify a portion (of time) of the data where the S2 sounds should occur. Also, the location of heart beats (such as by applying QRS complex data) can be used to help identify the location of S2 split in the data. Other data may also be imported to aid in the identification of the proper sounds, such as duration trend information as identified at block 508. If too little data is being obtained, the criteria used to analyze the data may be made less strict, and if too much data is being obtained, the criteria may be made more strict. Changing the strictness may occur automatically in response to meeting certain criteria, or may be manually adjusted by a user.

Once the data has been analyzed at blocks 501 and 502, the timing of the heart sounds, generally the timing of the sounds involved in the S2 split interval, can be determined at block 504. Since the timing of the data (the time at which the data—sounds—occur) is primarily being relied on for information instead of the amplitude of the data, this data may generally be less prone to noise-based artifacts than methods relying entirely on the amplitude of the data to obtain information.

The S2 split interval information obtained at block 504 can be analyzed to identify trends in the data at block 506. For instance, the heart rate may be four times as fast as the respiration rate (as may be typical). Thus, a trend of increasing data followed by decreasing data may be identified every four data sets. If the heart rate is not an integer of the respiration rate, slightly offset patterns of increasing and decreasing data may be seen. These trends may be used to determine the interval of a respiration cycle (or cycles).

The information obtained by analyzing the trends in the S2 interval may be used to determine respiration rate information at block 508. Respiration rate information could include the interval of a single respiration cycle or multiple cycles, the rate at which respiration is occurring, or other similar information.

Respiration rate may be determined by dividing the number of cycles being used by the total interval length of the cycles being used. For instance, the most recent 8 respiration cycles may be used to calculate a value, or each respiration cycle occurring within a certain amount of time (a minute, 30 seconds, 15 seconds, etc.) could be used. Alternatively, the respiration rate may be determined by counting the total number of respiration cycles occurring in a set period of time, and dividing by that time. Counting the number of respiration cycles can include counting the number of peaks in the data, or any other method of counting. Respiration rate may be determined from the respiration interval by any other means as well. If the respiration interval is known, then the respiration rate is also known. For purposes of this application, unless stated otherwise, reference to respiration rate also includes respiration interval.

Additionally, information relating to a patient may be used when calculating respiration rate. For example, young children may respire faster than adults so the age of the patient may affect the number of breaths used to generate a result. Additionally, for some patients it may be desirable to have a more stable respiration rate, so more breaths may be measured or a longer time period can be used. Alternatively, for other patients, it may be desirable to have a more reactive respiration rate so fewer breaths may be measured or a shorter time period may be used. This information can be input at block 510. This information may be received from a user or may be imported from a patient record, such as a medical record.

Other respiration related information may include determining that a patient is not breathing. This may be shown by respiration rate information that is flat or is not in a consistent pattern. This may include monitoring for apnea, when a patient stops breathing while their heart continues to beat. The two main types of apnea include central apnea and obstructive apnea. Central apnea indicates that the nerves that control breathing fail to function properly. Obstructive apnea indicates that some obstruction is preventing the transfer of gas from the environment to the lungs (and vice versa).

Figures 3, 4:
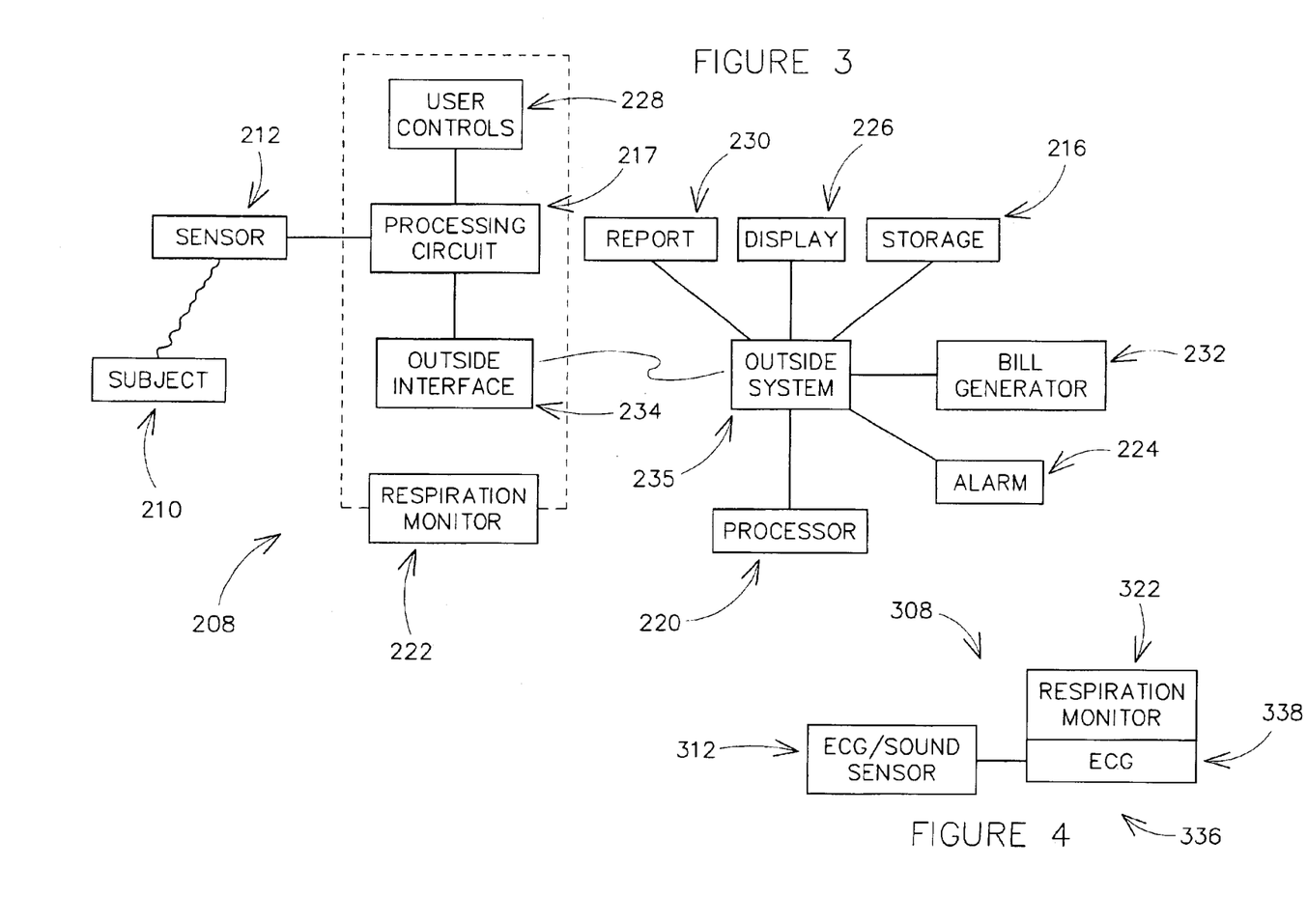
FIG. 3 is a schematic diagram of a monitoring system according to another embodiment.
FIG. 4 is a schematic diagram of a monitoring system according to another embodiment.

Referring to FIG. 3, a monitoring system 208 includes a sensor 212 that obtains information from a subject 210. Sensor 212 can be any number of sensors such as a acoustic sensor (e.g. a microphone) and an ultrasound sensor. Data from sensor 212 is transferred to respiration monitor 222. The data is received by processing circuit 217, which performs a function on the data. Processing circuit 217 can be configured to store the data; to process the data by filtering the data; to process the data by analyzing the data for patterns, for S2 split information, for trends, for respiration rate information, or for other information; or to process the data in some other manner.

Processing circuit 217 may include analog band pass filter circuitry 118 that produces a filtered heart sound signal based on a signal received from data input 114 and a microprocessor 120 configured to determine respiration rate based on the filtered heart sound signal. Also, processing circuit 217 may include a microprocessor that produces a filtered heart sound signal and/or that determines respiration rate based on a heart sound signal. The filter circuitry (whether analog or digital) can be configured to allow signals from about 100 Hz to about 500 HZ to pass. Alternatively, processing circuit 217 may include a data storage medium and control circuitry that facilitates storage of the data which has been inputted from the data input 114. Processing circuit 217 may include any number of other combinations of processing circuitry.

Processing circuit 217 may include various types of processing circuitry, digital and/or analog, and may include a microprocessor, microcontroller, application-specific integrated circuit (ASIC), or other circuitry configured to perform various input/output, control, analysis, and other functions to be described herein.

Respiration monitor 222 includes user controls 228 that allow a user to adjust various settings of respiration monitor 222. For instance, user controls 228 may be established to allow a user to change the information displayed, to select a mode of operation, to change the criteria used to analyze the data, to mark the occurrence of events (such as going to sleep and waking up), to input patient characteristics (like age) or may allow some other type of input.

Data from respiration monitor 222 can be transferred using an interface 234. Interface 234 could employ a physical data connection, or a wireless data connection. Further, interface 234 could be a network interface that allows data to be directly or indirectly transferred across a network. Additionally, interface 234 may be a physical data connection, such as a serial communication port, that allows data to be transferred from respiration monitor 222 to a computing device such as a portable or stationary computer, a tablet PC, a personal digital assistant (PDA), or other device.

If respiration monitor transfers data to an external system 235, the data may be transferred over a network, such as a local area network (LAN), a wide-area network (WAN), an intranet, and an internet. The network may be hardwired, may be wireless, or may be accessible from a dial-in or other access point. Some examples of hardwired systems include systems that use network cables, power lines, or other direct connections to form a network.

External system 235 may include a processor 220 that processes and/or analyzes the data from processing circuit 218. Processor 220 may be configured to perform any number of methods of analysis, and/or interpretation of the data.

External system 235 can also be coupled to a report generator 230, a data storage device 216, a record keeping device, additional processors, an alarm 224 and a display. Report generator 230 can generate a report based on data, data storage device 216 can store data, the record keeping device can make or add to a record based on data, and the display can display data acquired by a respiration monitor 222.

Additionally, a bill generator 232 can generate a bill based on the use of monitor 222. Bill generator 232 can generate a bill for the use of monitor 222, or can integrate the use of monitor 222 into a larger bill to be sent. Bill generator 232 can also monitor the usage of monitor 222, and generate reports based on usage of monitor 222. Bill generator 232 can also be used to send a notice to a person across a network indicating that monitor 222 is being used and billed, and/or that a patient is experiencing medical trouble. People that may desire receiving such a notice might include a patient's primary physician, a treating physician, an insurance carrier, and a patient. Delivering a notice to an insurance carrier may allow faster approval for sudden, unexpected usage of monitor 222, and/or other medical treatment. This would allow a hospital to collect funds sooner, and would allow a patient to worry less about obtaining coverage after treatment. This can also allow medical facility staff and insurance staff to make more informed business decisions. Once the bill is generated, it can then be sent physically or electronically to a recipient. The recipient may be a computer at an insurance company that calculates the extent of coverage and the amount to be paid based on the usage of monitor 222, or some other recipient.

Some embodiments of the invention may use relatively inexpensive sensors to form a respiration monitor. A lower cost respiration monitor may be useful for monitoring sub-acute patients. Sub-acute patients tend to be less critical than intensive care patients, and have a lower clinician to patient ratio. Some embodiments may also be useful as monitors that can be sent home with a patient such that data can be acquired when the patient is not in a health care facility, and then reviewed at a later point in time. This data may be transferred upon a subsequent visit to the health care facility, by a recording medium, over a network (such as the internet), or by other means. Still other embodiments may be used to form more complicated systems that monitor multiple parameters and/or more acutely monitor respiration, possibly using multiple techniques.

Referring to FIG. 4, a monitoring system may advantageously use both an ECG and a respiration monitor. At least two locations that are advantageous for placing a heart acoustic sensor, the left and the right sternal border at the fourth intercostal space of a patient, are also potential locations for an ECG electrode. Thus, an advantageous system may combine an ECG electrode and a acoustic sensor whereby only one probe need be attached to a patient to place both sensors. The data obtained by combined sensor probe 312 may be transmitted to monitor 336. Monitor 336 would be able to monitor one or both of respiration and ECG. Monitor 336 may further include circuits configured to process additional data, and/or to process the data from the acoustic sensor of combined sensor probe 312 to identify other abnormalities, such as heart abnormalities.

The invention has been described with reference to various specific and illustrative embodiments and techniques. However, it should be understood that many variations and modifications may be made while remaining within the spirit and scope of the invention. For instance many of the components and sub-components from sensors 112,212,312, respiration monitors 122,222,322, external system 235 and other listed components can be rearranged or removed and formed as a single unit, or as separate and distinct portions of the system and still remain within the scope of the invention.

What is claimed is:

1. A method comprising:
   obtaining heart sounds from a patient wherein the heart sounds are used to determine a duration of an S2 split; and
   determining respiration rate based on timing of the heart sounds and the duration of the S2 split;
   determining heart rate; and
   wherein determining respiration rate further comprises using the heart rate as a reference to identify the S2 split.

2. The method of claim 1, wherein obtaining heart sounds comprises inputting signals from an acoustic sensor positioned to detect heart sounds.

3. The method of claim 2, wherein the acoustic sensor from which signals are input is positioned at the left or right border of the sternum at about ICS-4.

4. The method of claim 2, the acoustic sensor is a piezo acoustic sensor.

5. The method of claim 1, further comprising determining heart rate based on the heart sounds.

6. The method of claim 5, further comprising determining heart rate variability based on the heart rate determination.

7. The method of claim 1, further comprising identifying a heart condition based on the heart sounds.

8. The method of claim 1, further comprising determining respiration rate using a technique not involving the use of heart sounds.

9. The method of claim 1, further comprising displaying information relating to the respiration rate.

10. The method of claim 1, further comprising transferring information relating to respiration rate across a network.

11. The method of claim 1, further comprising generating a bill based on use of a monitoring system used to determine respiration rate.

12. The method of claim 1, further comprising identifying patient conditions based on the determination of the respiration rate.

13. The method of claim 1, further comprising determining respiration rate based on changes in amplitude of the heart sounds.

14. The method of claim 1, wherein determining the respiration rate comprises identifying a pattern of a plurality of S2 split durations.

15. A method for determining respiration rate in a patient having an S2 split that depends on respiration phase, comprising:
    identifying a duration of an S2 split; and
    determining respiration rate based on the duration of the S2 split
    determining heart rate; and
    determining respiration rate further comprising using the heart rate as a reference to identify the S2 split.

16. The method of claim 15, wherein the duration of the S2 split is identified by detecting sounds caused by the closing of the aortic valve and the pulmonary valve.

17. The method of claim 15, wherein determining respiration rate comprises determining a rate based on a patient's characteristics.

18. The method of claim 15, further comprising displaying information relating to the respiration rate which has been determined.

19. The method of claim 18, wherein the information displayed includes the respiration rate.

20. The method of claim 15, further comprising generating an alarm based on durations of a plurality of S2 splits.

21. The method of claim 15, further comprising generating information for a patient record based on the determination of the respiration rate.

22. The method of claim 15, further comprising identifying patient conditions based on the determination of the respiration rate.

23. The method of claim 15, wherein determining the respiration rate comprises identifying a pattern of a plurality of S2 split durations.

24. The method of claim 15, further comprising identifying heart related conditions.

25. A method comprising:
    determining respiration rate based on timing of heart sounds of a patient;
    identifying occurrence of apnea based on the heart sounds; and
    identifying the type of apnea that has occurred.

26. The method of claim 25, further comprising determining heart rate based on the heart sounds.

27. The method of claim 25, further comprising generating information for a patient record based on the determination of the respiration rate.

28. The method of claim 25, further comprising displaying information relating to the apnea event which has been identified.

29. The method of claim 25, further comprising generating an alarm based on the respiration rate.

30. A medical monitoring system comprising:
    a data input configured to receive signals from a heart acoustic sensor, wherein the signals include heart sounds used to determine a duration of an S2 split; and
    a processing circuit configured to determine respiration rate based on the heart sounds and the duration of the S2 input from the heart acoustic sensor, the processing circuit further configured to determine heart rate, wherein determining the respiration rate includes using the heart rate as a reference to identify the S2 split.

31. The system of claim 30, further comprising a heart acoustic sensor.

32. The system of claim 31, wherein the heart acoustic sensor comprises a piezo acoustic sensor.

33. The system of claim 31, wherein the heart acoustic sensor further comprises an ECG electrode.

34. The system of claim 33, further comprising a processing circuit configured to process ECG signals.

35. The system of claim 34, wherein the processing circuit configured to process ECG signals is part of the same circuit as the processing circuit configured to determine respiration rate.

36. The system of claim 30, wherein the processing circuit comprises analog band pass filter circuitry configured to produce a filtered heart sound signal based on a signal received from the data input and a microprocessor configured to determine respiration rate based on the filtered heart sound signal.

37. The system of claim 36, wherein the band pass filter is configured to allow signals from about 100 Hz to about 500 HZ to pass.

38. The system of claim 30, wherein the processing circuit comprises a microprocessor configured to produce a filtered heart sound signal based on a signal received from the data input and configured to determine respiration rate based on the filtered heart sound signal.

39. The system of claim 30, wherein the processing circuit comprises a data storage medium and control circuitry configured to facilitate storage of data which has been inputted from the data input.

\* \* \* \* \*